(12) United States Patent
Lee et al.

(10) Patent No.: US 11,969,569 B2
(45) Date of Patent: Apr. 30, 2024

(54) MICRONEEDLE CARTRIDGE

(71) Applicant: JUBILEE BIOTECH CO., LTD., Wonju-si (KR)

(72) Inventors: Sung Kyoung Lee, Seoul (KR); Goonghyun Han, Siheung-si (KR)

(73) Assignee: JUBILEE BIOTECH CO., LTD., Wonju-si (KR)

( * ) Notice: Subject to any disclaimer, the term of this patent is extended or adjusted under 35 U.S.C. 154(b) by 238 days.

(21) Appl. No.: 17/547,167

(22) Filed: Dec. 9, 2021

(65) Prior Publication Data
US 2023/0181887 A1    Jun. 15, 2023

(51) Int. Cl.
*A61M 37/00*    (2006.01)

(52) U.S. Cl.
CPC . *A61M 37/0015* (2013.01); *A61M 2037/0023* (2013.01)

(58) Field of Classification Search
CPC ...... A61M 37/0015; A61M 2037/0023; A61M 2037/0061
See application file for complete search history.

(56) References Cited

U.S. PATENT DOCUMENTS

2010/0121271 A1* 5/2010 Perriere ............ A61M 5/14248
                                                          604/110
2013/0345638 A1   12/2013 Heidenreich et al.

FOREIGN PATENT DOCUMENTS

| JP | H1043296 A | 2/1998 |
| KR | 20100135863 A | 12/2010 |
| KR | 1020210106388 A | 8/2021 |
| KR | 102416058 B1 | 7/2022 |
| WO | 2021/167410 A1 | 8/2021 |

* cited by examiner

*Primary Examiner* — Amber R Stiles
(74) *Attorney, Agent, or Firm* — Rabin & Berdo, P.C.

(57) ABSTRACT

A microneedle cartridge according to the present disclosure includes a disk-shaped cartridge main body including a rotational force receiver configured to receive a rotational force from a microneedle applicator, a plurality of first through-holes radially disposed about the center of the cartridge main body, a plurality of microneedle bases each disposed in one of the first through-holes and having one or more microneedles disposed on a lower surface, a maintaining member configured to maintain the microneedle base inside the through-hole, and a second through-hole through which a pressing portion of the microneedle applicator passes when operating to seal the microneedle applicator, wherein the microneedle base is configured to be movable between a first position at which the microneedle base is not pressed by the pressing portion and a second position at which the microneedle base is maximally pressed by the pressing portion.

10 Claims, 10 Drawing Sheets

MICRONEEDLE CARTRIDGE

BACKGROUND

1. Field of the Invention

The present disclosure relates to a microneedle cartridge, and more particularly, to a microneedle cartridge capable of being replaceably mounted on a microneedle applicator used to puncture the skin with a microneedle and allowing a drug to be infused multiple times through different microneedles using a single cartridge.

2. Discussion of Related Art

Generally, infusing a drug into the skin is referred to as a transdermal drug delivery system. Since the transdermal drug delivery system does not involve the gastrointestinal tract, a drug can be administered regardless of the acidity of the gastrointestinal tract, enzymes in the gastrointestinal tract, food in the gastrointestinal tract, and movement of the gastrointestinal tract.

For the transdermal drug delivery system, ultrasonic waves, jet infusion, electroporation, iontophoresis, hypodermic needles, chemical penetration enhancers, microneedles, and the like are used.

Microneedles are fine needles having a length of hundreds of micrometers and deliver a drug component into the skin through the stratum corneum of the skin. A microneedle was developed by Mark Prausnitz in 1998 as a next-generation drug delivery system that combines a conventional syringe with the convenience of a patch to eliminate the fear of needles.

In addition to being able to deliver macromolecular substances such as proteins and peptides, microneedles have advantages such as enabling painless drug delivery, allowing faster recovery of the administration site as compared to general infusions, having a low risk of contamination and infection, and, due to their high effectiveness, allowing the amount of administered drug to be reduced. Accordingly, much research and development for the application of microneedles has taken place.

At an early stage, solid-type microneedles that form fine holes in the skin and allow a drug to penetrate into the skin through the formed holes were widely used. Such solid-type microneedles are still widely used by being processed into the form of a roller in the cosmetic industry.

Microneedles for subcutaneous infusion of drugs are classified into a coated type in which a surface of a needle is coated with a drug, a dissolving type in which a needle itself is formed with a material containing a drug component and the needle is dissolved in the skin, and a hollow type in which a drug is infused through a hollow inside a needle.

Except for the hollow type in which a drug storage is separately provided, the above microneedles are mostly provided on a patch on which an adhesive for adhesion to the skin is applied and are used in the form of being attached to the skin.

Regardless of whether the microneedle is the hollow type or the patch type which substitutes for an infusion needle, microneedles have been distributed only for one-time use so far.

While one infusion is sufficient for medicines such as vaccines, most drugs require repeated administration at predetermined time intervals. Thus, there is an inconvenience of having to carry an applicator for hollow-type microneedles all the time or replace an attached patch at predetermined time intervals.

Accordingly, through International Unexamined Patent Application Publication No. WO 2021/167410, the present applicant has disclosed a microneedle applicator and a cartridge that allow a drug to be periodically infused using a microneedle.

The cartridge disclosed in the previous invention of the present applicant is formed in a disk shape and has a microneedle base disposed in each of a plurality of through-holes radially disposed along the circumference. A microneedle is formed on a lower surface of the microneedle base.

The applicator of the previous invention is operated using a method in which, when the cartridge is mounted, a pressing portion in the applicator moves to above the cartridge to press a selected microneedle into the skin.

In this case, since the vertically-moving pressing portion should be rotated, the configuration of the applicator becomes complex, and it is difficult to reduce the size of the applicator when manufacturing the applicator in the form of a wearable device.

Due to development of an applicator in which a pressing portion only moves vertically and a cartridge rotates to press a microneedle, a cartridge suitable therefor is necessary.

RELATED ART DOCUMENT

Patent Document

International Unexamined Patent Application Publication No. WO 2021/167410 (Date of Publication: Aug. 26, 2021)

SUMMARY OF THE INVENTION

The present disclosure is directed to providing a microneedle cartridge that is suitable for an applicator in which a pressing portion only moves vertically and a cartridge rotates to press a microneedle.

The present disclosure is also directed to providing a microneedle cartridge capable of minimizing damage to a puncture site caused by repeated puncturing using a microneedle.

The present disclosure is also directed to providing a microneedle cartridge that is suitable for securing a waterproof function of a microneedle applicator.

The present disclosure is also directed to providing a microneedle cartridge capable of disinfecting a portion of a microneedle that is inserted into the skin.

A microneedle cartridge according to the present disclosure includes a disk-shaped cartridge main body including a rotational force receiver configured to receive a rotational force from a microneedle applicator, a plurality of first through-holes radially disposed about the center of the cartridge main body, a plurality of microneedle bases each disposed in one of the first through-holes and having one or more microneedles disposed on a lower surface, a maintaining member configured to maintain the microneedle base inside the through-hole, and a second through-hole through which a pressing portion of the microneedle applicator passes when moving to seal the microneedle applicator, wherein the microneedle base is configured to be movable between a first position at which the microneedle base is not pressed by the pressing portion and a second position at which the microneedle base is maximally pressed by the pressing portion.

A position of the microneedle disposed on the lower surface of the microneedle base may be different from a position of another microneedle disposed on a lower surface of an adjacent microneedle base.

A drug delivered by the microneedle may be different from a drug delivered by an adjacent microneedle.

The maintaining member may have an elastic force and allow the microneedle base to return from the second position to the first position.

The microneedle cartridge may further include a thin film adhered to upper and lower surfaces of the cartridge main body to seal the first through-hole.

The maintaining member may be a member configured to connect the microneedle base to an inner wall of the first through-hole.

The maintaining member may be a thin film adhered to an upper surface of the cartridge main body.

The thin film on the upper surface or the lower surface of the cartridge main body may have an elastic force and allow the microneedle base to return from the second position to the first position.

Some of the first through-holes may be filled with a disinfectant.

A wiper may be installed between the first through-holes on a lower surface of the microneedle cartridge.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, embodiments of the present disclosure will be described in detail with reference to the accompanying drawings.

Figure 1:
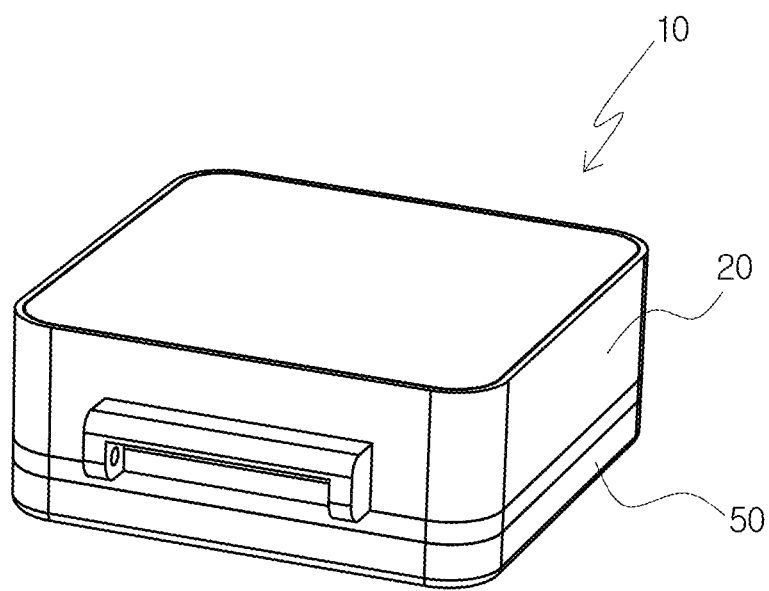
FIG. 1 is a view illustrating the form of a microneedle applicator according to the present disclosure.
Figure 2:
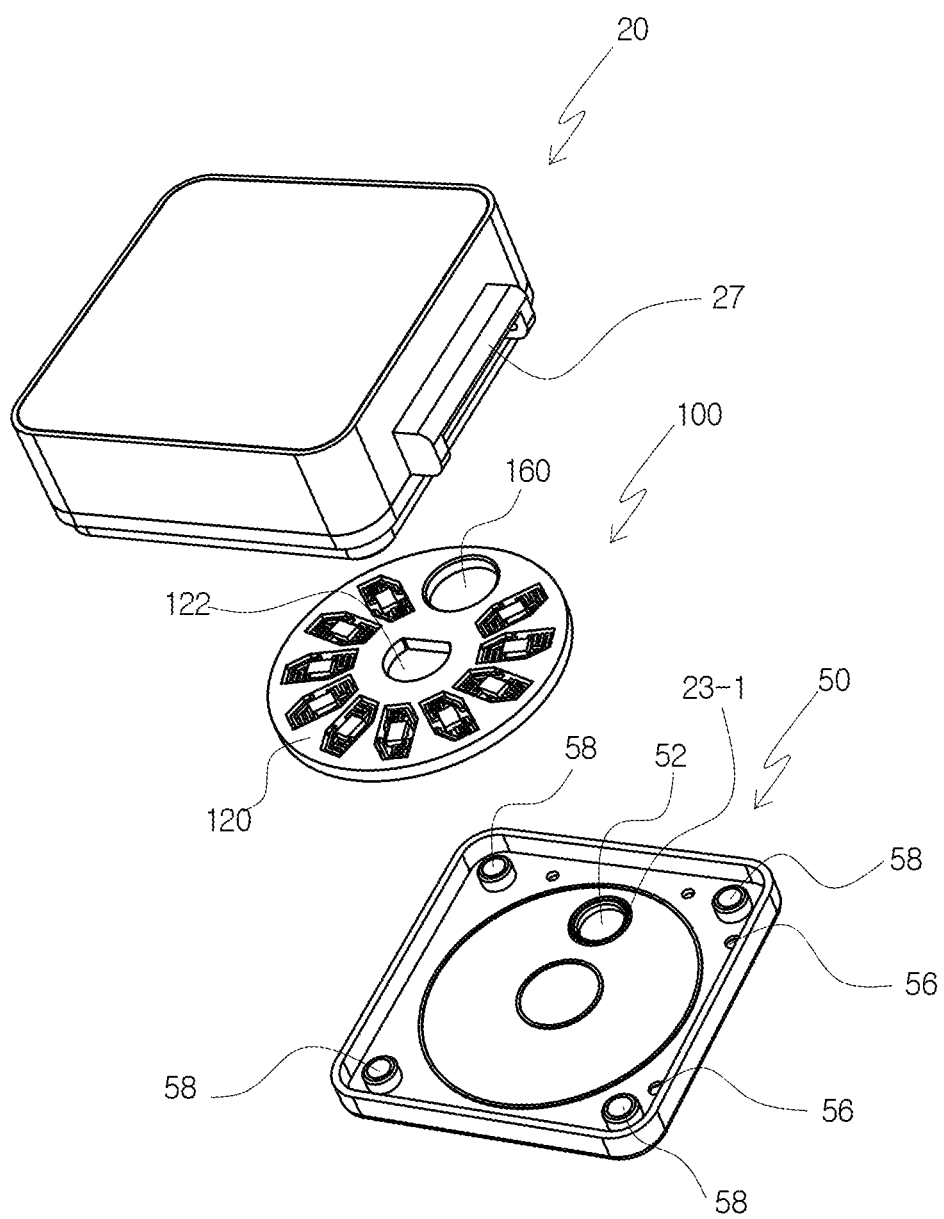
FIG. 2 is an exploded perspective view of the microneedle applicator viewed from the top.
Figure 3:
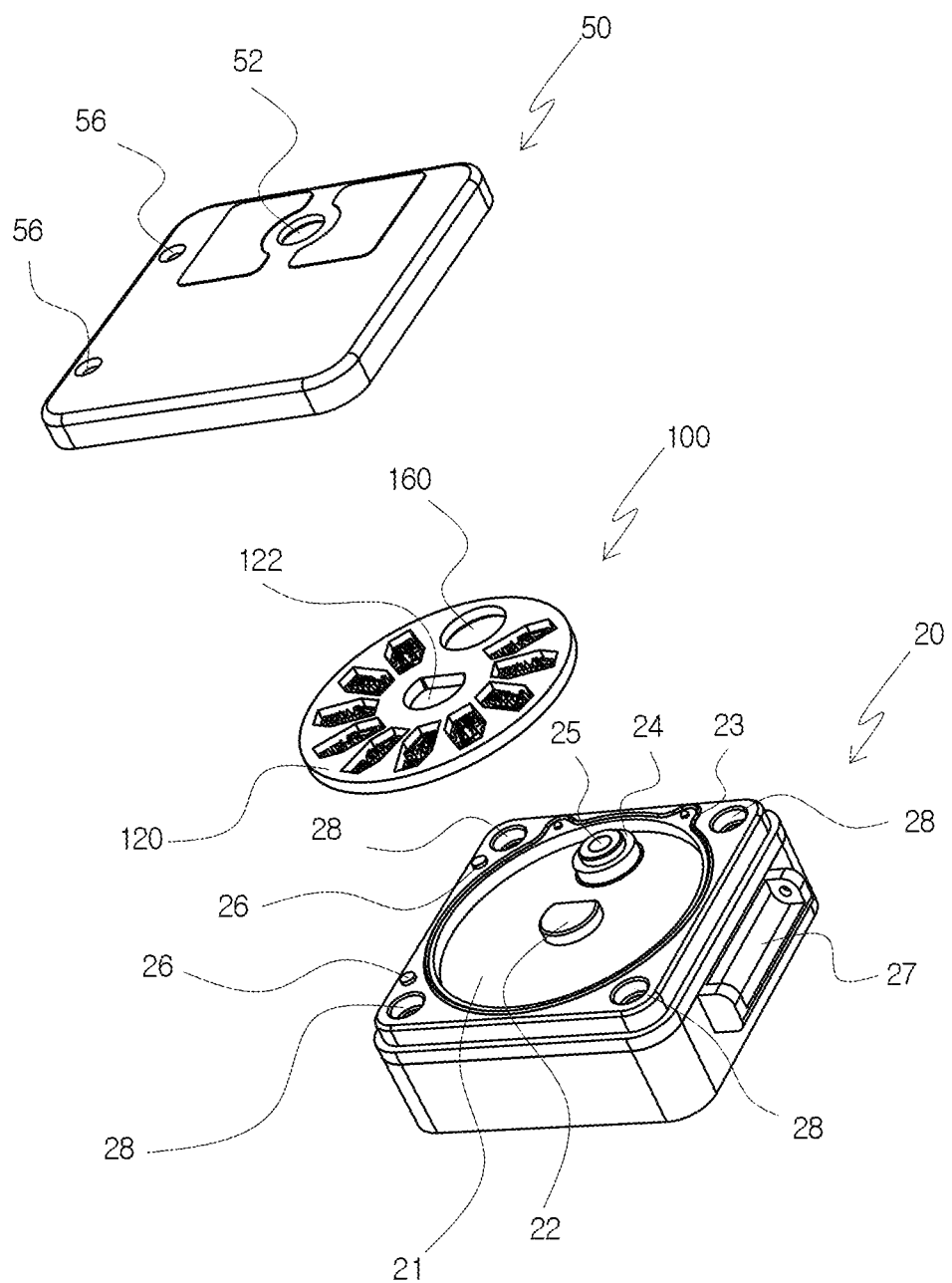
FIG. 3 is an exploded perspective view of the microneedle applicator viewed from the bottom.

FIG. 1 is a perspective view illustrating an exterior of a microneedle applicator according to the present disclosure, FIG. 2 is an exploded perspective view of the microneedle applicator viewed from the top, and FIG. 3 is an exploded perspective view of the microneedle applicator viewed from the bottom.

A microneedle applicator 10 includes an applicator main body portion 20 and a bottom portion 50 detachably coupled to a lower surface of the applicator main body portion 20.

A microneedle cartridge 100 is inserted into a space between the bottom portion 50 and the lower surface of the applicator main body portion 20.

A controller configured to control operation of the microneedle applicator, a rechargeable battery configured to supply power, and a driver configured to operate according to a command of the controller are installed inside the applicator main body portion 20, and pressing portions 24 and 25 reciprocate by moving toward or away from the bottom portion according to the operation of the driver.

A cartridge coupling shaft 22 coupled to rotate the microneedle cartridge 100 is exposed from the lower surface of the applicator main body portion 20.

A cartridge insertion groove 21 and a charging terminal 26 are disposed on the lower surface of the applicator main body portion 20, and a sealing portion 23 is disposed along an outer boundary of the cartridge insertion groove 21.

A strap mounting portion 27 for mounting a strap that allows the microneedle applicator to be worn around the wrist is disposed in the applicator main body portion 20 of the present embodiment.

The applicator main body portion 20 and the bottom portion 50 include coupling portions 28 and 58 coupled to each other by a magnetic force.

A pressing portion coupling hole 52 to which the pressing portions 24 and 25 that have passed through a second through-hole 160 of the microneedle cartridge 100 are coupled and a charging terminal hole 56 configured to expose the charging terminal 26 to the outside are provided in the bottom portion 50.

Figure 5A:
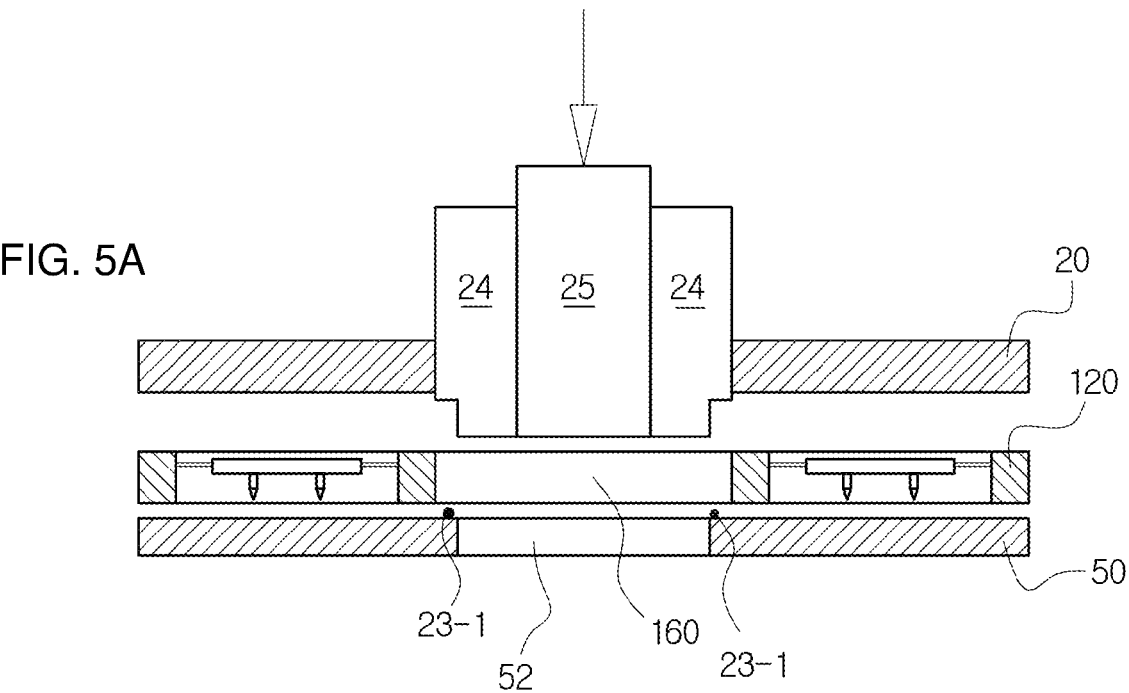
FIGS. 5A and 5B are views illustrating the relationship between a pressing portion and a pressing portion coupling hole according to the present disclosure.
Figure 5B:
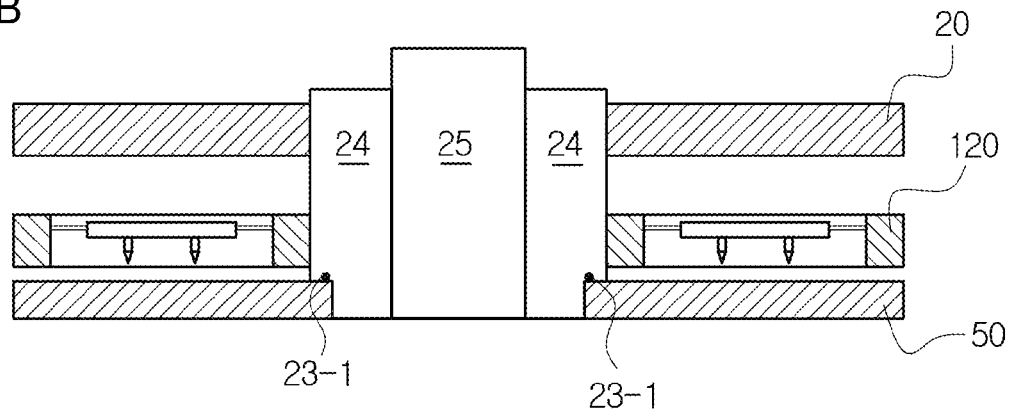

When the microneedle applicator 10 does not operate, as illustrated in FIG. 5B, the pressing portions 24 and 25 move downward through the second through-hole 160 and are coupled to the pressing portion coupling hole 52.

When a cartridge main body 120 rotates during the operation of the microneedle applicator 10, the pressing portions 24 and 25 move upward as illustrated in FIG. 5A.

The sealing portion 23 is disposed near the pressing portion coupling hole 52 to, in cooperation with the pressing portion 24, make the applicator main body portion 20 waterproof.

A lower surface of the bottom portion 50 comes into contact with the user's skin when the microneedle applicator is worn by the user.

The cartridge main body 120 is formed in a disk shape and includes a rotational force receiver 122 configured to receive a rotational force from the microneedle applicator 10.

In the present embodiment, the rotational force receiver 122 is formed at the center of the cartridge main body 120 so as to be coupled to the cartridge coupling shaft 22. However, the rotational force receiver may also be provided as a gear that is machined on a side surface constituting a circumferential surface of the disk-shaped cartridge main body 120, and a driving gear engaged with the gear, instead of the cartridge coupling shaft 22, to apply a rotational force to the microneedle cartridge 100 may be provided.

A plurality of first through-holes 150 are radially installed about the center of the cartridge main body 120.

A microneedle base 170 is disposed in each first through-hole 150, and a microneedle 175 is disposed on a lower surface of the microneedle base 170.

Figure 4:
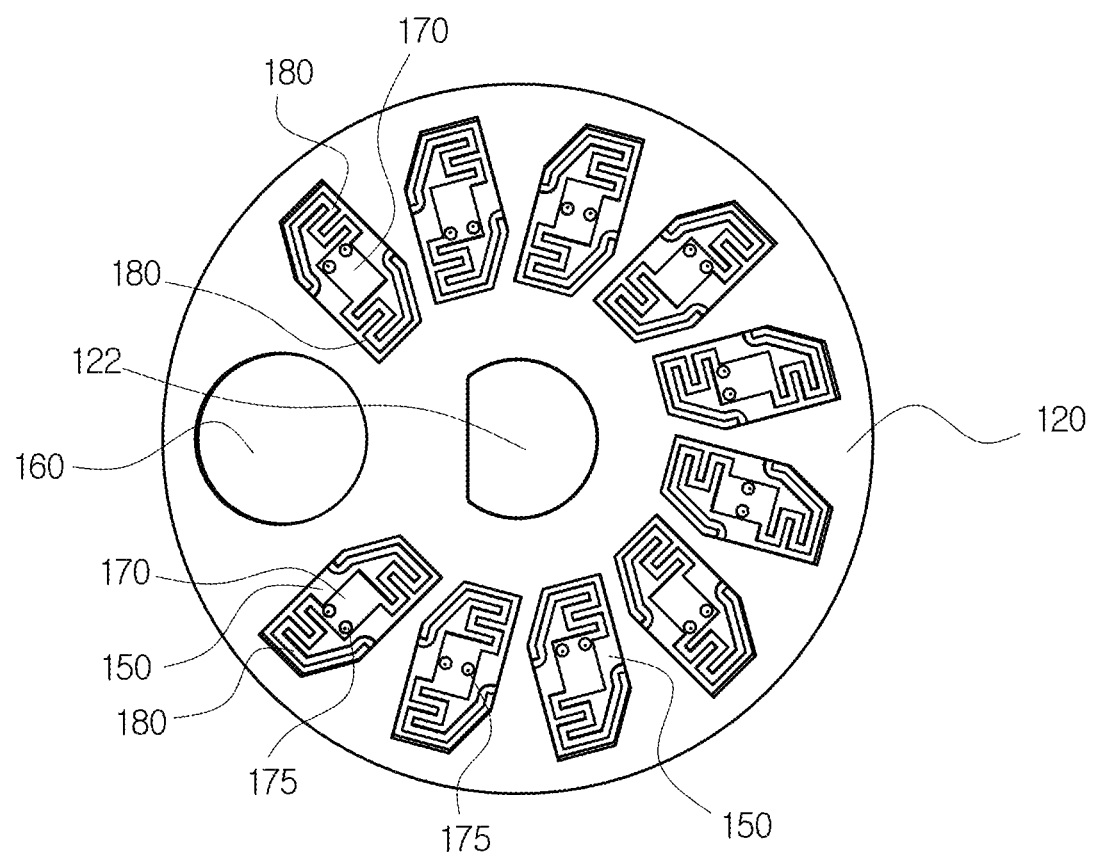
FIG. 4 is a bottom view of a microneedle cartridge according to another embodiment of the present disclosure.

The same number of microneedles 175 may be disposed at the same positions on the lower surfaces of respective microneedle bases 170. However, as illustrated in FIG. 4, the microneedles 175 on adjacent microneedle bases 170 may also be formed at different positions thereon.

Generally, the skin punctured by a microneedle is known to return to its original state after about four hours. When the time during which a drug is infused using microneedles is within four hours, in order to avoid skin damage, the microneedles may be disposed at different positions as illustrated in FIG. 4.

The microneedle base 170 of the present disclosure is connected to an inner wall of the first through-hole 150 by a maintaining member 180. The maintaining member 180 serves to, when the pressing portion 25 of the microneedle applicator presses the microneedle base 170 toward the skin, maintain the microneedle base 170 to prevent the microneedle base 170 from being detached from the microneedle cartridge 100.

Also, the maintaining member 180 serves to provide an elastic force that allows the microneedle base 170 to return from a second position, at which the microneedle base 170 is maximally pressed toward the skin by the pressing portion 25, to its original position (a first position) in the first through-hole 150.

The maintaining member 180 of the present embodiment connects the microneedle base 170 to the inner wall of the first through-hole 150.

Figure 6A:
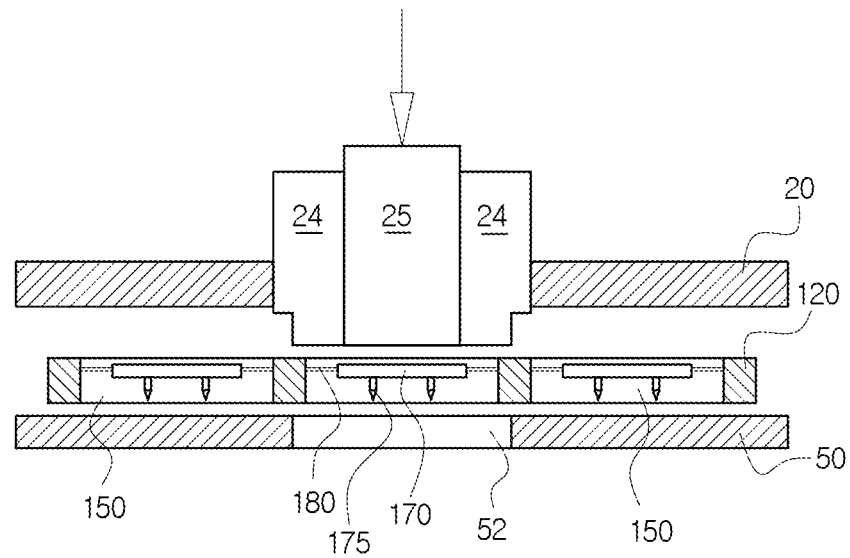
FIGS. 6A to 6C, 7, 8A and 8B are views illustrating the relationship between the pressing portion and the microneedle cartridge.
Figure 6B:
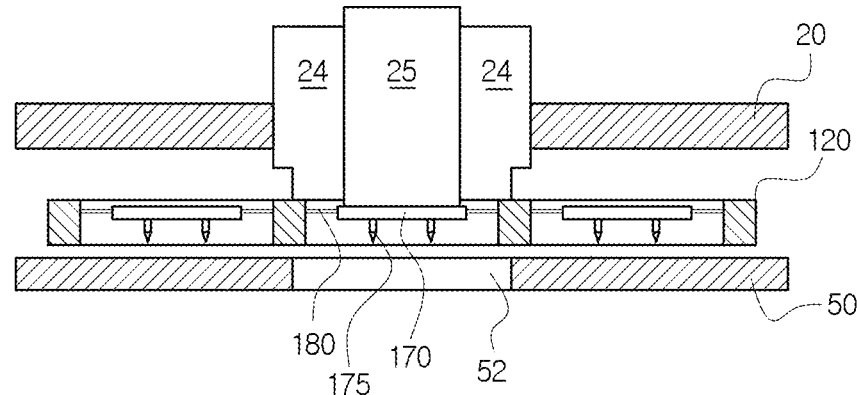
Figure 6C:
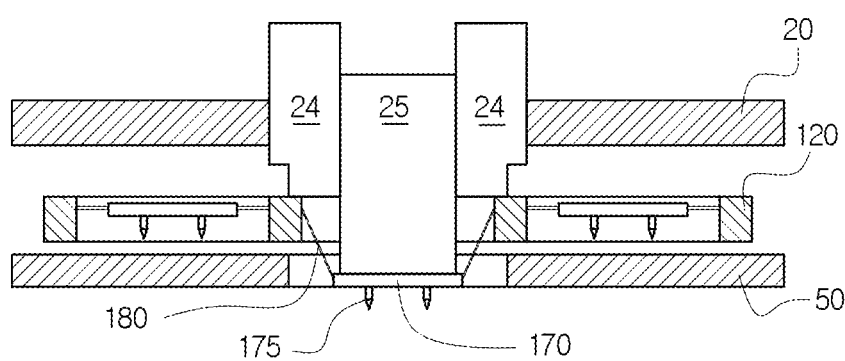

When, as illustrated in FIG. 6A, the microneedle cartridge rotates and thus the microneedle base 170 for infusing a drug is disposed at lower ends of the pressing portions 24 and 25, as illustrated in FIG. 6B, the pressing portions 24 and 25 move downward and press the cartridge main body 120 and the microneedle base 170. Then, the pressing portion 25 further moves downward, and thus, as illustrated in FIG. 6C, the microneedle base 170 reaches the second position at which the microneedle base 170 is maximally pressed, and the microneedle 175 is completely inserted into the skin.

When drug infusion using the microneedle 175 is completed, the pressing portions 24 and 25 move upward, and due to elasticity of the maintaining member 180, the microneedle base 170 returns to the position illustrated in FIG. 6A.

A thin film is adhered to upper and lower surfaces of the microneedle cartridge to prevent contamination of the microneedle base 170 and the microneedle 175 in the first through-hole 150.

The thin film may be made of various materials such as a synthetic resin. Although the thin film is not illustrated in the drawings of the present application unless otherwise indicated, those of ordinary skill in the art should understand the attachment position, form, etc. of the thin film.

Figure 7:
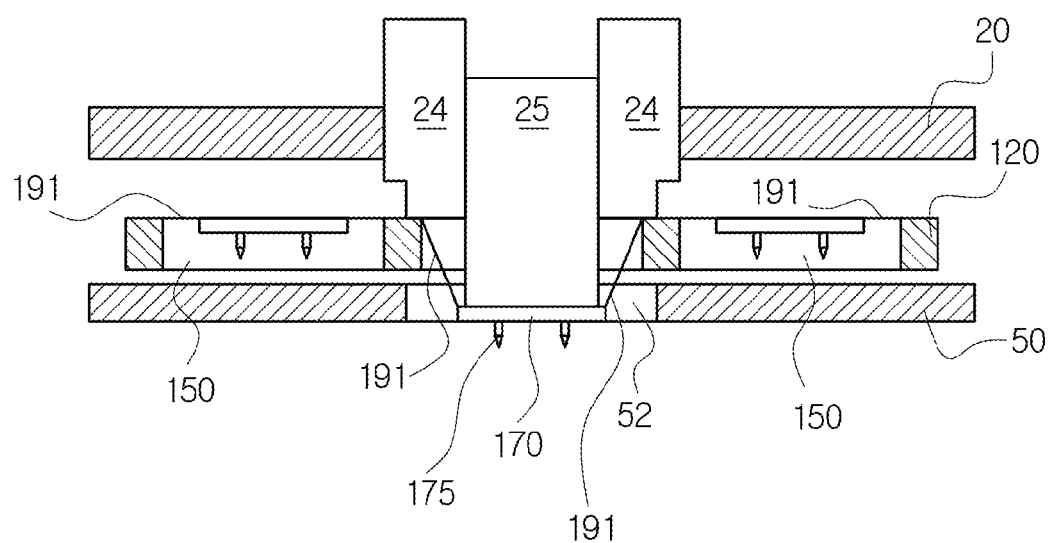

FIG. 7 illustrates a state in which, when the microneedle base 170 is attached to a thin film 191, which is adhered to the upper surface of the microneedle cartridge, and pressed by the pressing portion 25, the thin film 191 is stretched to the second position without tearing. Then, due to an elastic force of the thin film 191, the microneedle base 170 may return to the first position.

Figure 8A:
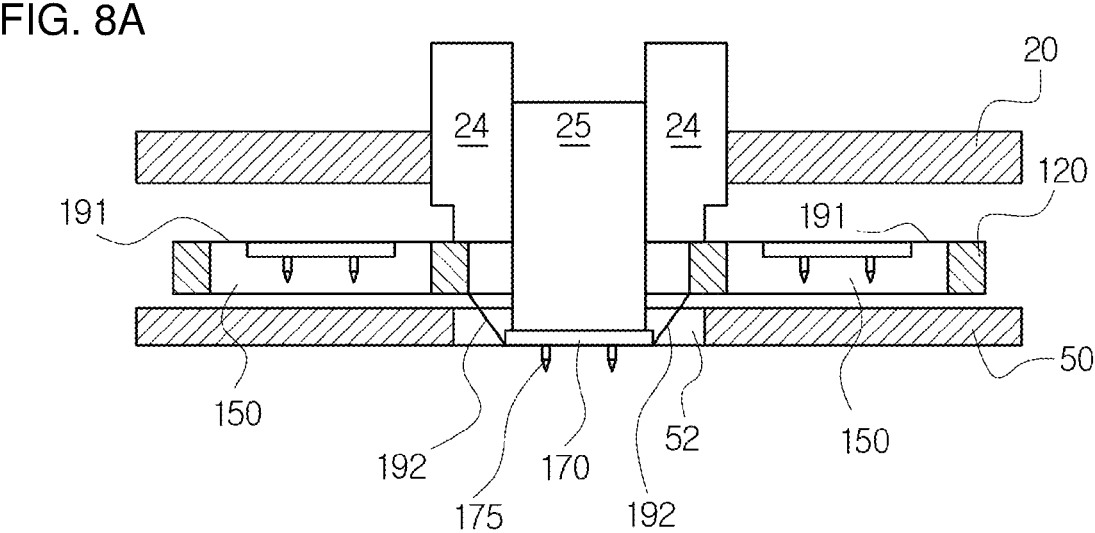
Figure 8B:
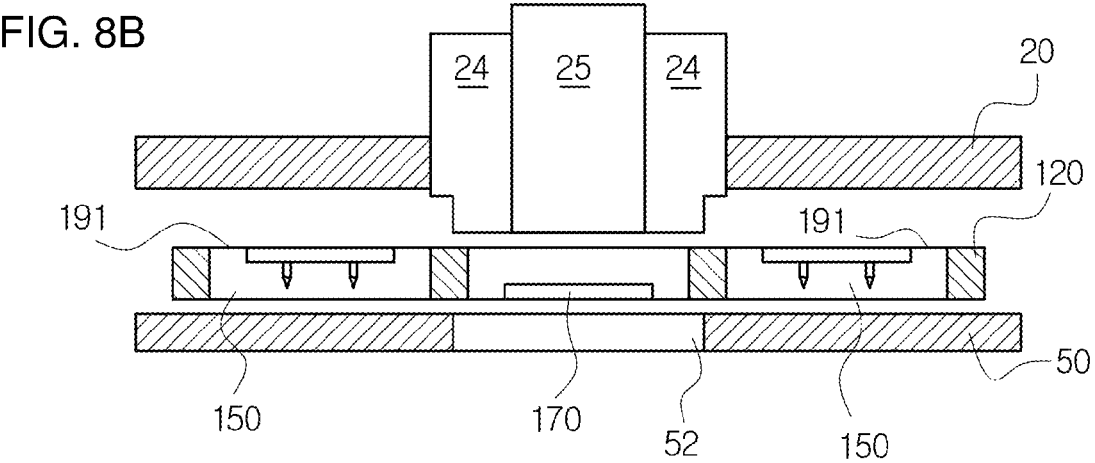

An embodiment of FIG. 8 is the same as the embodiment of FIG. 7 in that the microneedle base 170, which is attached to the thin film 191 adhered to the upper surface of the microneedle cartridge, is pressed by the pressing portion 25. The embodiment of FIG. 8 is different from the embodiment of FIG. 7 in that a thin film 192 attached to the lower surface of the microneedle cartridge is stretched to the second position. FIG. 8B illustrates a state in which the microneedle base 170 is returned to the first position due to an elastic force of the thin film 192 attached to the lower surface of the microneedle cartridge.

Figure 9:
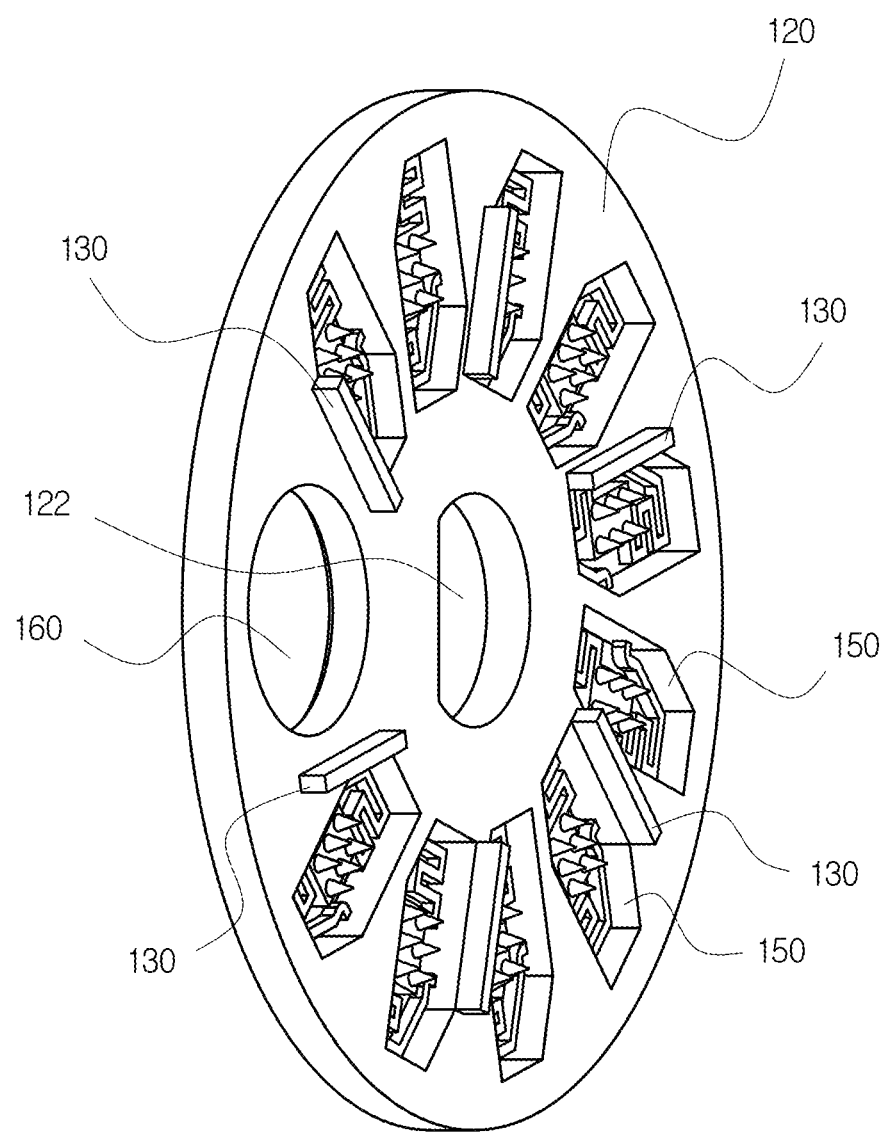
FIG. 9 is a view illustrating the microneedle cartridge having a wiper attached thereto.

FIG. 9 illustrates a wiper 130 installed between the first through-holes 150 on a lower surface of the cartridge main body 120, and FIG. 10 is a view illustrating the operational relationship between a disinfectant 140 and the wiper 130.

Figure 10A:
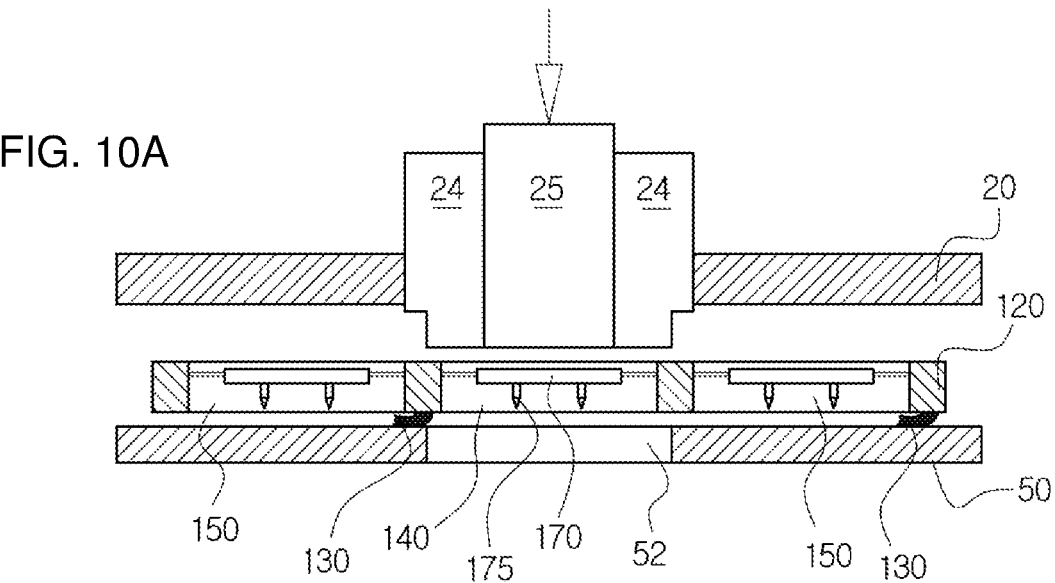
FIGS. 10A to 10C are views illustrating the operational relationship between a disinfectant and the wiper.
Figure 10B:
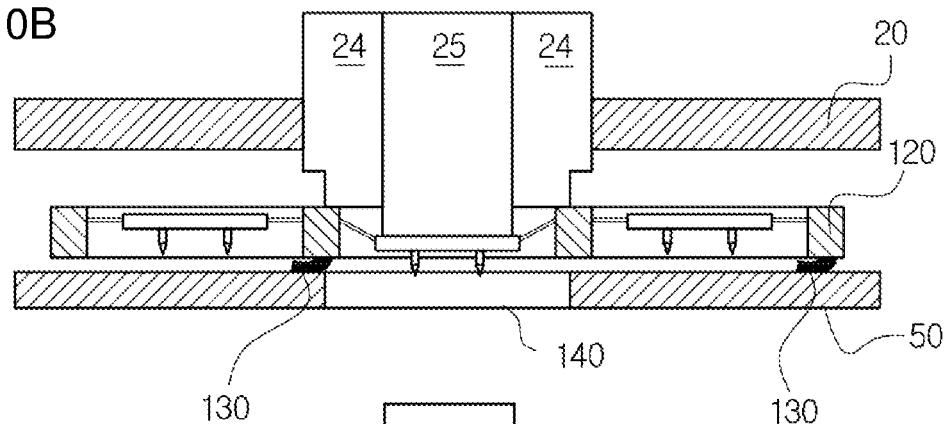

FIG. 10A illustrates a state in which a first through-hole 150-1 disposed at the center is filled with the disinfectant 140. When the pressing portions 24 and 25 move downward and press the microneedle base 170, and thus the thin film 192 on the lower surface of the microneedle cartridge 100 is perforated, the disinfectant 140 in the first through-hole 150-1 leaks toward the skin (see FIG. 10B).

Here, it is not necessary for the microneedle base 170 to move to the second position, preferably the microneedle base 170 may only move to the extent that causes the thin film 192 to be perforated, and microneedle 175 in the first through-hole 150-1 does not coated with drugs nor be dissolved with be disinfectant 140

Figure 10C:
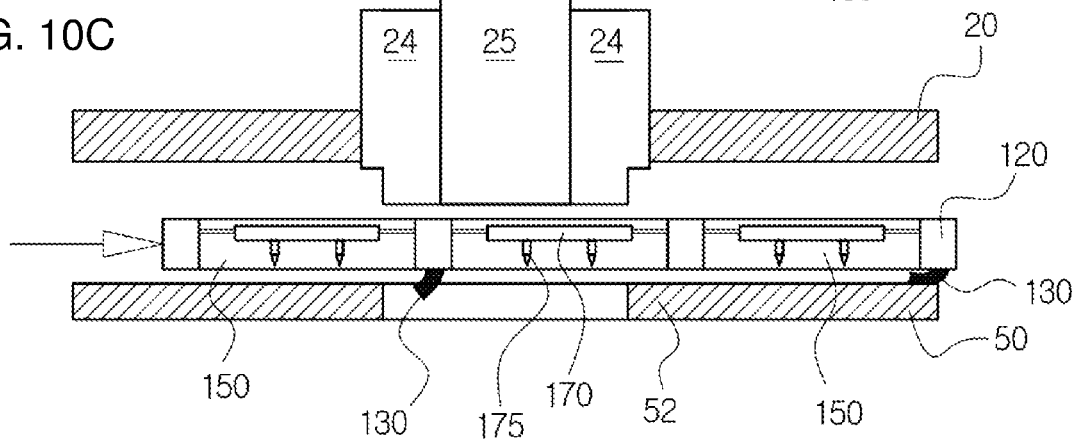

After the thin film 192 is perforated, when the pressing portions 24 and 25 and the microneedle base 170 move upward, and the cartridge main body 120 continues to rotate, the wiper 130 disinfects the skin surface in cooperation with the disinfectant 140 in the pressing portion coupling hole 52 (see FIG. 10C). The wiper 130 may be made of a flexible material such as rubber, silicone, and fiber materials.

Then, the microneedle 175 in a first through-hole 150-2 adjacent to the first through-hole 150-1 moves to below the pressing portions 24 and 25.

According to the present disclosure having the above-described configurations, it is possible to provide a microneedle cartridge that is suitable for an applicator in which a pressing portion only moves vertically and a cartridge rotates to press a microneedle. The microneedle cartridge of the present disclosure is suitable for securing a protection function of a microneedle applicator against water and dust.

The microneedle cartridge of the present disclosure can minimize damage to a puncture site caused by repeated puncturing using a microneedle and can disinfect a portion of a microneedle that is inserted into the skin.

The above description is only for exemplary description of the technical spirit of the present disclosure, and those of ordinary skill in the art to which the present disclosure pertains may make various modifications and changes within the scope not departing from essential characteristics of the present disclosure.

Therefore, the embodiments disclosed herein are for describing the technical spirit of the present disclosure instead of limiting the same, and the scope of the technical spirit of the present disclosure is not limited by the embodiments. The scope of the present disclosure should be interpreted by the claims below, and all technical spirits within the scope equivalent thereto should be interpreted as falling within the scope of the present disclosure.

What is claimed is:
1. A microneedle cartridge comprising:
   a disk-shaped cartridge main body including a rotational force receiver configured to receive a rotational force from a microneedle applicator;
   a plurality of first through-holes radially disposed about a center of the cartridge main body;
   a plurality of microneedle bases each disposed in one of the first through-holes and having one or more microneedles disposed on a lower surface thereof;
   a maintaining member configured to maintain each microneedle base inside each one of the first through-holes; and a second through-hole through which a pressing portion of the microneedle applicator passes when moving to seal the microneedle applicator, wherein each microneedle base is configured to be movable between a first position at which said each microneedle base is not pressed by the pressing portion and a second position at which said each microneedle base is maximally pressed by the pressing portion.

2. The microneedle cartridge of claim 1, wherein a position of the one or more microneedles disposed on a lower surface of one of the plurality of microneedle bases is different from a position of another one or more microneedles disposed on a lower surface of an adjacent one of the plurality of microneedle bases.

3. The microneedle cartridge of claim 1, wherein a drug delivered by the one or more microneedles is different from a drug delivered by an adjacent microneedle.

4. The microneedle cartridge of claim 1, wherein the maintaining member has an elastic force and allows each microneedle base to return from the second position to the first position.

5. The microneedle cartridge of claim 1, further comprising a thin film adhered to upper and lower surfaces of the cartridge main body to seal the plurality of first through-holes.

6. The microneedle cartridge of claim 5, wherein the thin film on the upper surface or the lower surface of the cartridge main body has an elastic force and allows each microneedle base to return from the second position to the first position.

7. The microneedle cartridge of claim 1, wherein the maintaining member is a member configured to connect each microneedle base to an inner wall of its first through-hole.

8. The microneedle cartridge of claim 1, wherein the maintaining member is a thin film adhered to an upper surface of the cartridge main body.

9. The microneedle cartridge of claim 1, wherein some of the first through-holes are filled with a disinfectant.

10. The microneedle cartridge of claim 1, wherein a wiper is installed between the first through-holes on a lower surface of the microneedle cartridge.

* * * * *